United States Patent
Li et al.

(10) Patent No.: US 10,005,727 B2
(45) Date of Patent: Jun. 26, 2018

(54) COMPOUND AND ANALOGUES FOR TRACING HISTONE ACETYLATION INHIBITORS PET IMAGING FOR DIAGNOSIS AND TREATMENT OF TUMORS

(71) Applicants: Ming-Hsin Li, Taoyuan (TW); Chyng-Yann Shiue, Taoyuan (TW); Han-Chih Chang, Taoyuan (TW); Chun-Fang Feng, Taoyuan (TW)

(72) Inventors: Ming-Hsin Li, Taoyuan (TW); Chyng-Yann Shiue, Taoyuan (TW); Han-Chih Chang, Taoyuan (TW); Chun-Fang Feng, Taoyuan (TW)

(73) Assignee: INSTITUTE OF NUCLEAR ENERGY RESEARCH ATOMIC ENERGY COUNCIL EXECUTIVE YUAN, Taoyuan (TW)

( * ) Notice: Subject to any disclaimer, the term of this patent is extended or adjusted under 35 U.S.C. 154(b) by 0 days. days.

(21) Appl. No.: 15/286,596

(22) Filed: Oct. 6, 2016

(65) Prior Publication Data

US 2018/0099933 A1 Apr. 12, 2018

(51) Int. Cl.
C07D 209/04 (2006.01)
C07D 401/12 (2006.01)
C07D 401/14 (2006.01)

(52) U.S. Cl.
CPC ......... C07D 209/04 (2013.01); C07D 401/12 (2013.01); C07D 401/14 (2013.01)

(58) Field of Classification Search
CPC .................................................. C07D 209/04
USPC .......................................................... 548/491
See application file for complete search history.

(56) References Cited

U.S. PATENT DOCUMENTS

2012/0263848 A1* 10/2012 Born .................... C07D 209/08
426/537

OTHER PUBLICATIONS

Dorwa;d et al., Side Reactions in Organic Synthesis, 2005, Wiley: VCH Weinheim Preface, pp. 1-15 and Chapter 8, pp. 279-308.*

* cited by examiner

*Primary Examiner* — Patricia L Morris
(74) *Attorney, Agent, or Firm* — Ming Chow; Sinorica, LLC

(57) ABSTRACT

The present invention relates to a group of compounds for nuclear medicine imaging through F-18 labeled histone acetylation inhibitors (HDACi) of indole or indoline benzoyl amine and its derivatives, and provides a series of nuclear medicine imaging agents that bind with HDAC overexpression in vivo for diagnosis of malignant tumors discovered in the nuclear medicine imaging tracing.

7 Claims, No Drawings

COMPOUND AND ANALOGUES FOR TRACING HISTONE ACETYLATION INHIBITORS PET IMAGING FOR DIAGNOSIS AND TREATMENT OF TUMORS

BACKGROUND OF THE INVENTION

Field of the Invention

The present invention relates to PET imaging compounds and analogues for tracing histone deacetylases inhibitor (HDACi) for tumor diagnosis and therapy, and more particularly to compounds of nuclear medicine imaging tracer which is capable of binding in vivo for use in the diagnosis of malignancy disease responses.

Description of Related Art

According to the statistics, in the year of 2014, Taiwan's top ten causes of death is led by malignant tumors in 33 consecutive years, the death toll was 46,095 people, accounting for 28.3% of all deaths. The current treatment of cancer can be divided into, drug therapy, surgical resection and radiation therapy. For drug treatment, although the general effect of chemotherapy drugs to kill cancer cells is powerful, but side effects of poisoned normal cells also exist, so in recent years, the major international pharmaceutical companies are fully committed to the development of drugs for targeted cancer cells. Among them, "HDAC inhibitor" is one of the popular development projects. Histone deacetylase (HDACs) is an important enzyme involved in the epigenetic regulation of histone deacetylases (HATs), which regulates the acetylation of chromatin histones. The two types of enzymes determine the degree of histone acetylation, cell growth, apoptosis, aging and so on.

Once the activity of HDACs is abnormally increased, the degree of protein acetylation will be out of balance, which will affect the activity of tumor suppressor genes in vivo, for example, the tumor suppressor genes, such as p53, causing cancers to grow, such as brain cancer, breast cancer, pancreas cancer. HDACs can be divided into four subtypes, a total of 11 kinds of Isoenzymes. According to the literature that many organs, such as colon, rectum, cervix, stomach and prostate, that suffer from malignant tumors and developmental disorders are found excessive HDAC-2 performance in the study.

Histone deacetylase inhibitors (abbreviated as HDAC inhibitors or HDACi) are medication for controlling histone deacetylase in the human body and being used to treat cancer and neurodegeneration by medical industries in medical research. Vorinostat (suberoylanilide hydroxamic acid, SAHA) and Romidepsin (cyclic peptide) are approved to be listed for applying to cutaneous T-cell lymphoma (CTCL) and the application of the treatment of solid tumor is also in clinical trials. The benzoylamide HDAC inhibitors chidamide developed by Chipscreen Ltd. is approved by FDA for clinical research in USA to confirm that the new type HDAC inhibitors in small doses and low concentration can induce tumor cell differentiation and selective apoptosis for anti-tumor proliferation and be non-toxic to normal cells.

The diagnosis of tumor is important in determining whether the tumor, the nature of the tumor to be benign or malignant, the stage of the malignancy, and the presence or absence of metastasis. Tumors are often found late. At this point it has damaged vital organs of one or more functions, and even has been transferred to the body. Therefore, the key issue in the treatment of cancer is how to detect the tumor at early time, however a early detection of malignant tumors is still very difficult.

Clinical diagnosis with imaging inspection includes X-ray examination, ultrasonography, magnetic resonance imaging, X-ray tomography (abbreviated as CT) and radioisotope examination. Early diagnosis of tumor disease has a role of important significance, because only a early diagnosis and treatment can get better result of treatment. However, due to various objective and subjective reasons, the majority of patients in the treatment or diagnosis of tumors that already advanced in midterm or later, and the treatment effect is not satisfactory in this case. Although the diagnosis method of tumor is developing rapidly, but many tumor screening methods are not effective enough, and it takes that tumors need to be of 1~1.5 cm in diameter size before it can be clearly displayed in an imaging inspection.

General blood test accuracy is insufficient, for example, a prostate-specific antigen (PSA) is a glycoprotein. This antigen can only be produced by prostate cells, when a prostate disease occurs, such as prostate tumor, a prostate hyperplasia cell will produce an excess of PSA that leads to the PSA level in the blood increases. Doctors may analyze blood PSA levels to determine the possibility of patients suffering from a prostate tumor. There are various factors leading to elevated PSA, such as prostate infection and benign prostate hyperplasia. Moreover, not all prostate cancer patients exhibited elevated PSA, thus a PSA test result could not be confirmed for a candidate of prostate cancer patient.

HDAC inhibitor (abbreviated as HDACi) is a drug that inhibits the function of deacetylase in the body's tissue proteins. HDACi can inhibit the activity of HDACs, promote cancer cell apoptosis, thereby achieving the purpose of mitigation or treatment of cancer.

The current treatment of cancer can be divided into, drug therapy, surgical resection and radiation therapy, the drug treatment, although the general effect of chemotherapy drugs to kill cancer cells powerful, but will also be poisoned with normal cells, side effects. Histone deacetylase (HDAC) inhibitors as a new generation of targeted anti-tumor drugs, has become a hot drug research. The existing HDAC inhibitors can be divided into: (1) hydroxamic acids including Vorinostat, etc.; (2) cyclic tetrapeptides including Romidepsin (FK228) and depsipeptides; (3) benzamides include MS-275 and SC-027; (4) short-chain fatty acids: including valproic acid, butyric acid and so on. The therapeutic effect of HDAC inhibitors on hematologic malignancies and solid tumors has been demonstrated in both in vivo and in vitro assays.

In vitro assays demonstrate that HDAC inhibitors exhibit good antitumor effects on a variety of tumor cells, including the bladder, bone, breast, uterus, central nervous system, esophagus, lung, ovary, pancreas, prostate, etc., which can make these tumor cells apparent of cell apoptosis, proliferation inhibition, and cell cycle arrest. A variety of HDAC inhibitors because of its multi-channel anti-cancer has entered the stage of anti-tumor treatment or phase I or II or III clinical studies.

SUMMARY OF THE INVENTION

The primary object of the present invention is to provide an advanced nuclear medicine imaging tracer technique for HDAC inhibitor, including Inno-IBM and its 23 analogues, is used to produce a series of novel nuclear medicine imaging tracers through binding to the histone deacetylase that is overexpressed in vivo.

Another object of the present invention is to provide novel chemical compounds for diagnosis of cancer by using the characteristic of positron decay of isotope F-18 to cause an annihilation reaction that makes positrons released from positron decay encountering electrons of cells to form a pair of opposed directions gamma rays for gaining images through positron emission tomography (PET).

The present invention is to provide the HDAC inhibitor labeled with radionuclide F-18 that comprises Inno-IBM and its 23 analogues, the structural formula 1 of which is shown below. The symbol X in the formula 1 stands for N or C.

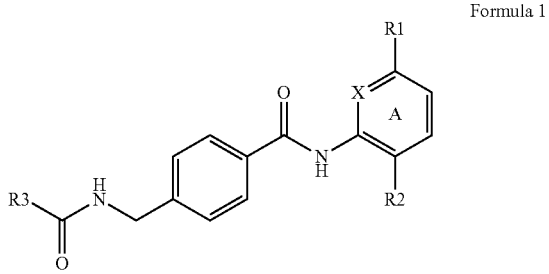

Formula 1

The present invention is to provide HDAC inhibitor labeled with radionuclide F-18 that comprises Inno-IBM and its 23 analogues as shown in table 1 below.

TABLE 1

| Name | A | R1 | R2 | R3 |
|---|---|---|---|---|
| INNO-IBM | (phenyl ring with R1, NH, R2) | F-phenyl-CH3 | NH2 | indoline |
| INNO-IBM-a | (pyridine ring with R1, NH, R2) | F-phenyl-CH3 | NH2 | indoline |
| INNO-IBM-b | (pyridine ring with R1, NH, R2) | F-pyridine-CH3 | NH2 | indoline |
| INNO-IBM-c | (phenyl ring with R1, NH, R2) | phenyl-CH3 | HN-CH3, CH2CH2F | indoline |
| INNO-IBM-d | (phenyl ring with R1, NH, R2) | phenyl-CH3 | HN-CH3, CH2-C≡C-F | indoline |

TABLE 1-continued

| Name | A | R1 | R2 | R3 |
|---|---|---|---|---|
| INNO-IBM-e | 2-amino-pyridine with R1, R2 | tolyl | HN(CH₃)CH₂CH₂F | indoline |
| INNO-IBM-f | aniline with R1, R2 | tolyl | NH₂CH₃ | indoline |
| INNO-IBM-g | 2-amino-pyridine with R1, R2 | tolyl | NH₂CH₃ | indoline |
| INNO-IBM-h | aniline with R1, R2 | 2-methylpyridyl | NH₂CH₃ | indoline |
| INNO-IBM-i | aniline with R1, R2 | 2-fluoro-5-methylphenyl | HN(CH₃)CH₂CH₂CH₃ | indoline |
| INNO-IBM-j | aniline with R1, R2 | 2-fluoro-5-methylphenyl | HN(CH₃)CH₂C≡CCH₃ | indoline |
| INNO-IBM-k | 2-amino-pyridine with R1, R2 | tolyl | HN(CH₃)CH₂CH₂CH₃ | indoline |

TABLE 1-continued

| Name | A | R1 | R2 | R3 |
|---|---|---|---|---|
| INNO-IBM-l | 2,5-disubstituted aniline (R1, R2, NH) | 4-fluorophenyl (with methyl) | CH₂NH₂ | indole |
| INNO-IBM-m | 2,3-disubstituted 6-aza (pyridine, R1, R2, NH) | 4-fluorophenyl (with methyl) | CH₂NH₂ | indole |
| INNO-IBM-n | 2,5-disubstituted pyridine (R1, R2, NH) | 3-fluoro-6-methylpyridine | CH₂NH₂ | indole |
| INNO-IBM-o | 2,5-disubstituted aniline (R1, R2, NH) | 2-methylphenyl | CH₂-NH-CH₂CH₂F | indole |
| INNO-IBM-p | 2,5-disubstituted aniline (R1, R2, NH) | 2-methylphenyl | CH₂-NH-CH₂-C≡C-F | indole |
| INNO-IBM-q | 2,3-disubstituted pyridine (R1, R2, NH) | 2-methylphenyl | CH₂-NH-CH₂CH₂F | indole |
| INNO-IBM-r | 2,5-disubstituted aniline (R1, R2, NH) | 2-methylphenyl | CH₂NH₂ | indole |

TABLE 1-continued

| Name | A | R1 | R2 | R3 |
|---|---|---|---|---|
| INNO-IBM-s | 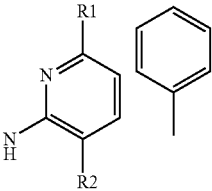 |  | 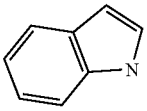 | 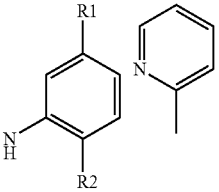 |
| INNO-IBM-t |  | 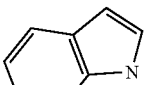 | 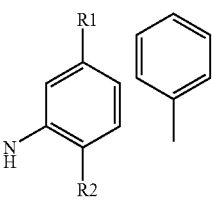 |  |
| INNO-IBM-u | 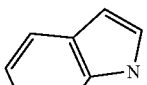 | 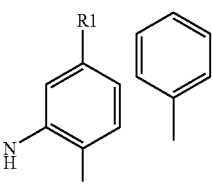 |  | 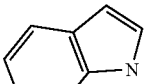 |
| INNO-IBM-v | 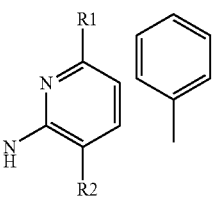 | | | |
| INNO-IBM-w |  | | | |

DETAILED DESCRIPTION OF THE PREFERRED EMBODIMENTS

The invention is a nucleus imaging tracer technology for HDAC inhibitor, including indole/indoline-benzamide derivative and its 23 kinds of derivative labeled with radionuclide F-18, a series of novel nuclear medicine imaging tracers are produced, which are used to combine with the overexpression of histone deacetylase in the body. The related reaction and mechanism of the syntheses of the present invention are shown in the Formula 2 and described below:

Formula 2

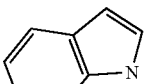

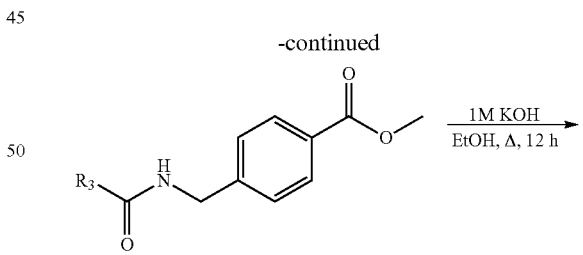

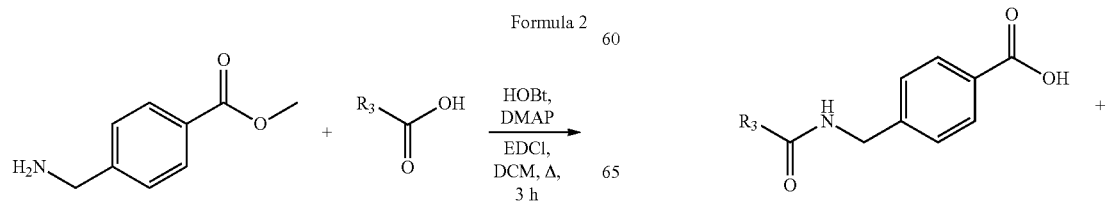

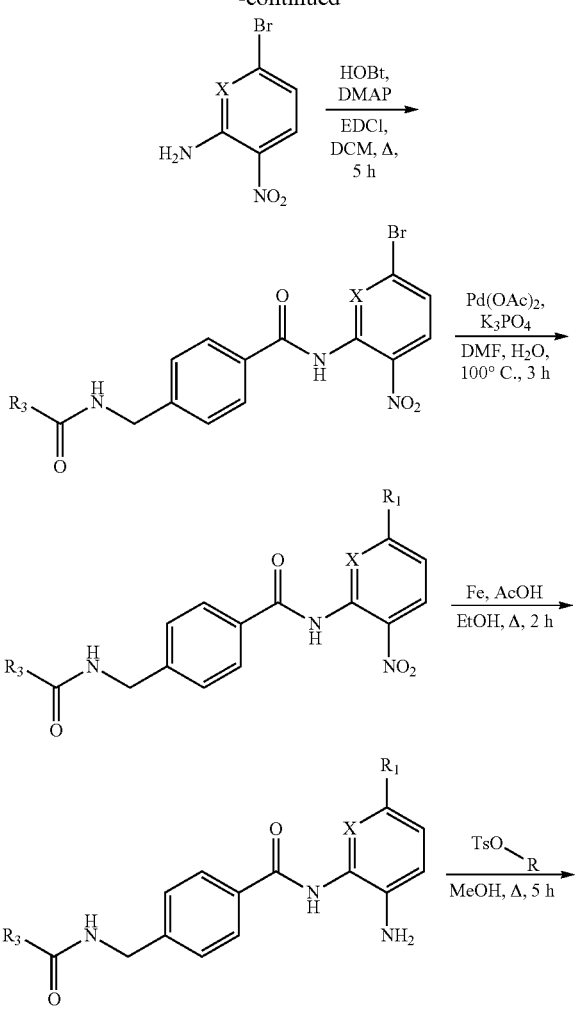

R1 = benzene, 4-fluorobenzene, 3-fluoropyridine
R2 = NH2, 2-fluoroethanamine, 4-fluorobut-2-yn-1-amine
R3 = indole, indoline
X = N, C The chemical reaction of Formula 2 is described in detail below.

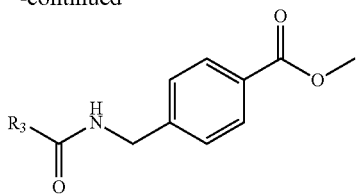

Using the coupling reagents HOBt, DMAP and EDCI to perform SN2 nucleophilic substitution reaction for the carboxylic acid and the amine in the dehydrated DCM (dichloromethane) aprotic solvents. In order to improve the reaction yield, DCM must be heated for boiling in the reaction process, the reaction time is about three hours. R3 is indole or indoline.

Using strong base (1M KOH) to deprotect ester and bare carboxylic acid group in the solvent of ethanol. The reaction should be heated slowly for heating too fast will lead to over-reaction. The reaction time is about 12 hours overnight.

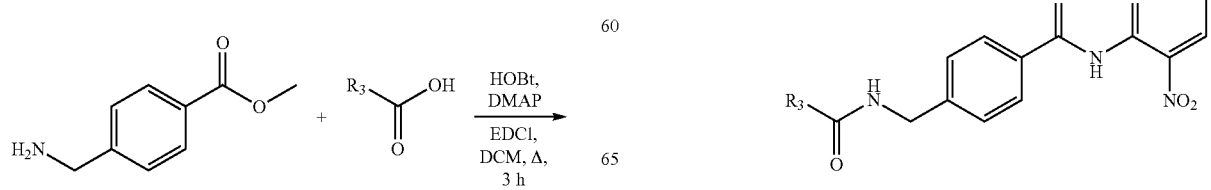

Using the coupling reagents HOBt, DMAP and EDCI to perform SN2 nucleophilic substitution reaction for the carboxylic acid and the amine in the dehydrated DCM (dichloromethane) aprotic solvents. The reaction time is about five hours. X is a nitrogen atom (N) or a carbon atom (C).

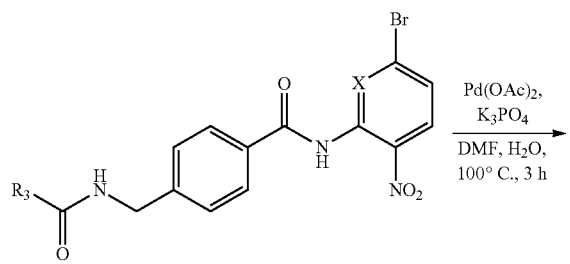

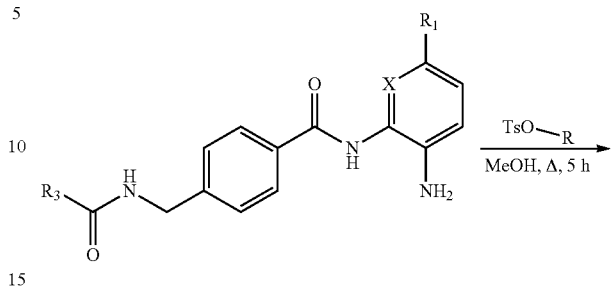

The Suzuki coupling reaction is carried out using palladium metal and inorganic salts in DMF and water. The reaction must be heated to 100 degree C. for about three hours. R1 is benzene or 4-fluorobenzene or 3-fluoropyridine.

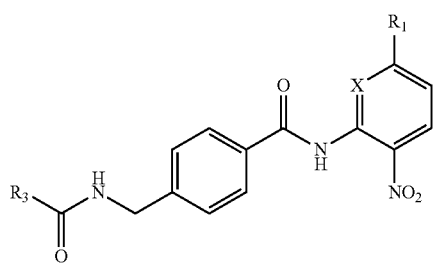

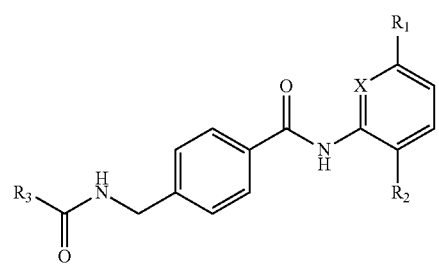

TsO is a group very easy to leave and easy to carry out SN1 nucleophilic substitution reaction. In order to improve the reaction yield, the reaction process needs to be heated to methanol boiling. The reaction time is about 5 hours. R2 is $NH_2$ or 2-fluoroethanamine or 4-fluorobut-2-yn-1-amine.

In the formula 2, R1 represents phenyl, 4-fluorophenyl, or benzenepyridine; R2 represents an amino group ($NH_2$),

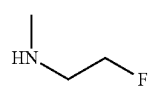

or

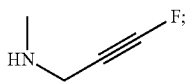

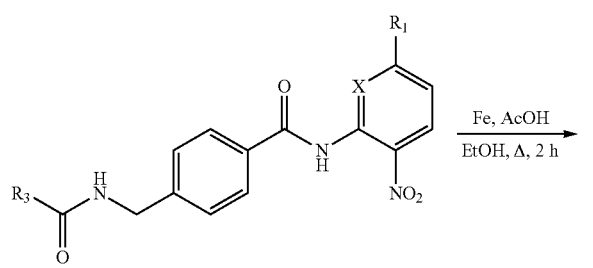

Using iron powder and acetic acid to reduce nitro ($NO_7$) into amine ($NH_2$). In order to improve the reaction yield, the reaction process needs to be heated to ethanol boiling. The reaction can be observed when the nitro yellow will slowly change to amine brown. The reaction requires close monitoring for preventing from overreaction.

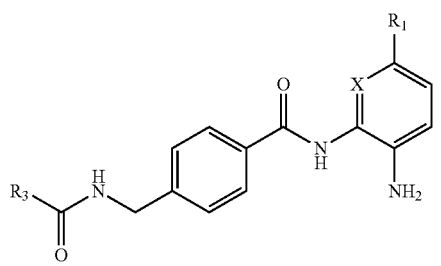

R3 represents Indole or Indoline; X represents nitrogen (N) or carbon (C). The reactants include 1-hydroxy-1,2,3-benzotriazole (HOBt), 4-Dimethylaminopyridine (DMAP), N-(3-dimethylaminopropyl)-N'-ethylcarbodiimide hydrochloride (EDCI), dichloromethane (DCM) ethyl acetate (EtOAc), acetic acid (AcOH), potassium hydroxide (KOH), Methyl alcohol (MeOH).

The produce of R1, R2 and R3 in the above Formula 2 is shown in Table 2 below.

TABLE 2
| R | Group | Chemical Reaction Formula | Reaction Name |
|---|---|---|---|
| R1 | Benzene | 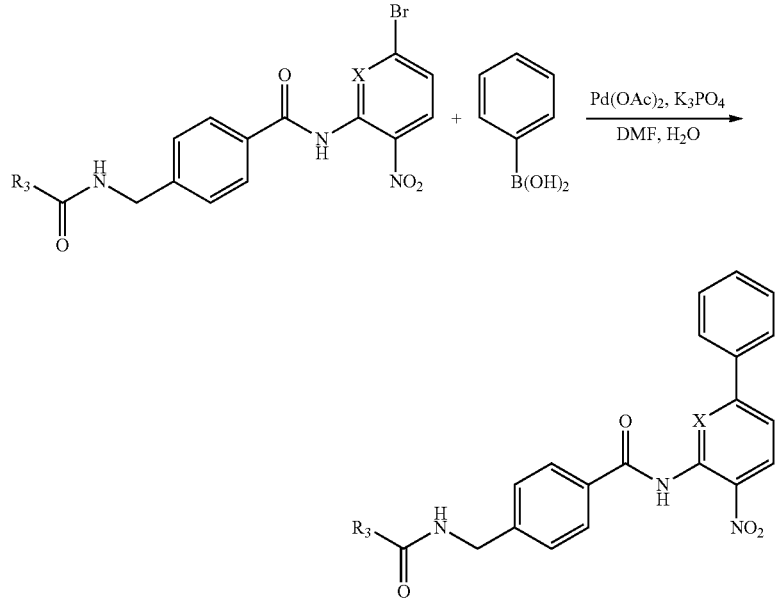 | Suzuki coupling (benzene boronic acid with the benzene ring a halogen cross-coupling) |
| | 4-fluorobenzene | 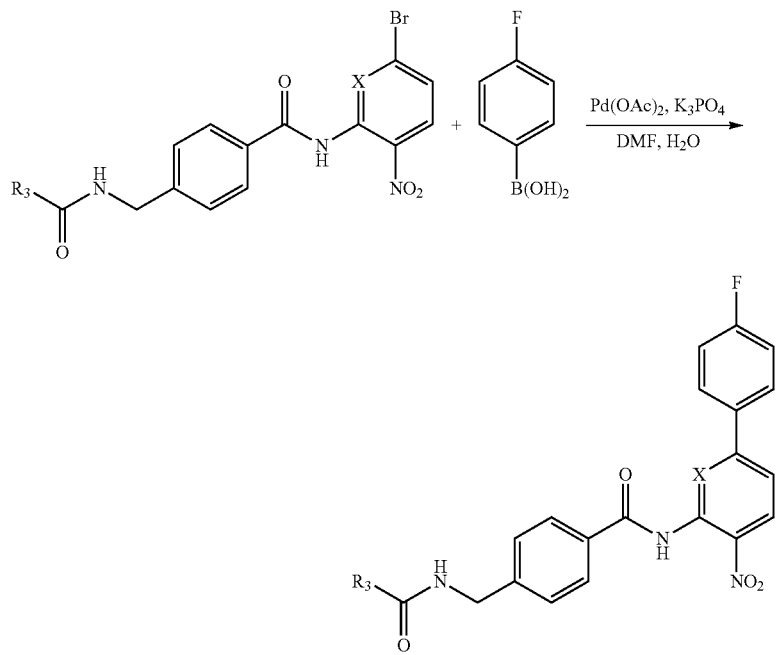 | Suzuki coupling |
| | 4-fluoropyridine | 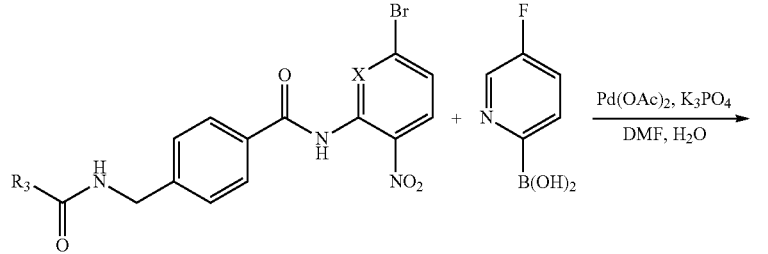 | Suzuki coupling |

TABLE 2-continued
| R | Group | Chemical Reaction Formula | Reaction Name |
|---|---|---|---|
| | | 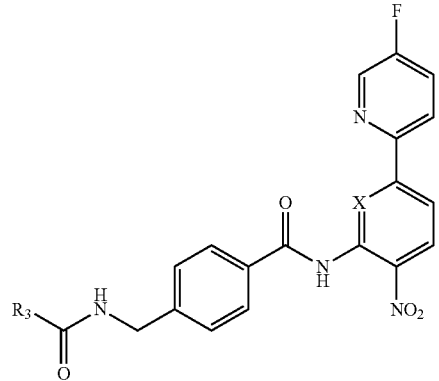 | |
| R2 | NH2 | 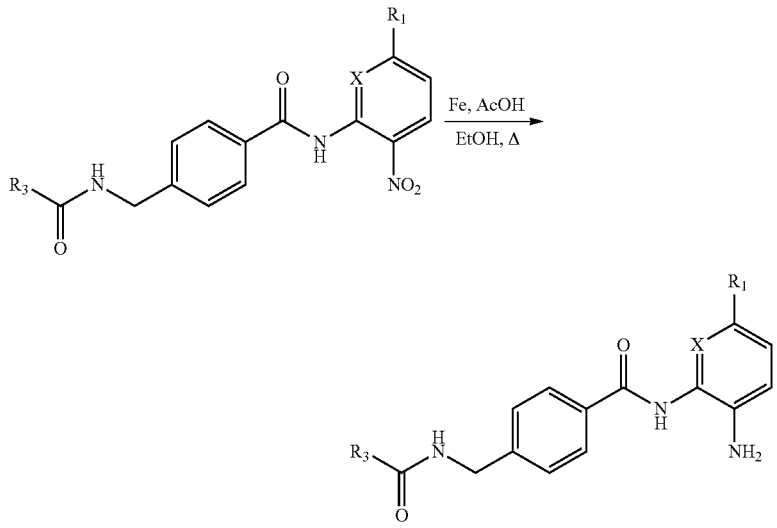 | Iron reduction |
| | 2-fluoroethanamine | 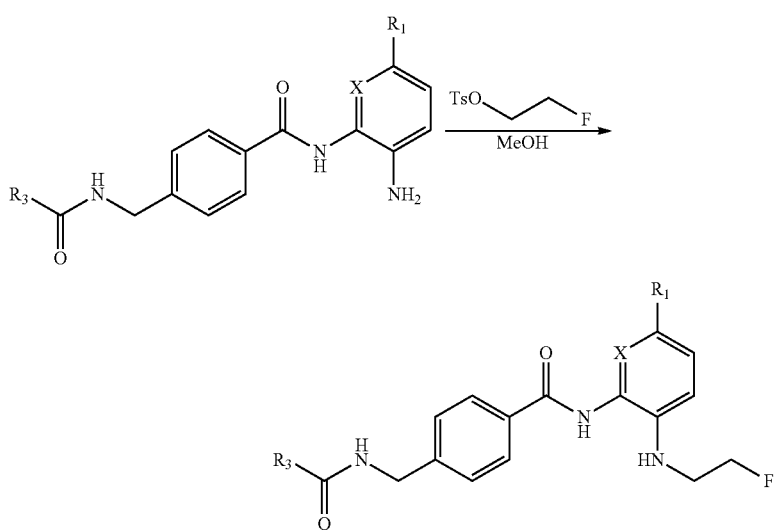 | Nucleophilic substitution |

TABLE 2-continued
| R | Group | Chemical Reaction Formula | Reaction Name |
|---|---|---|---|
|  | 4-fluorobut-2-yn-1-amine | 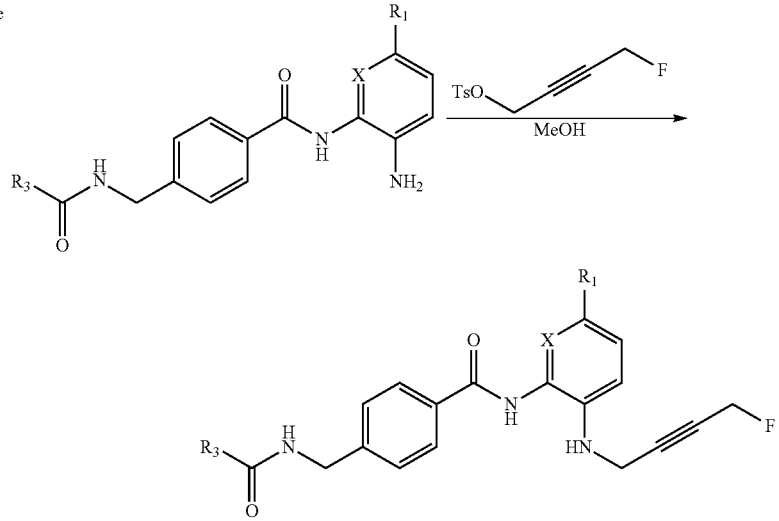 | Nucleophilic substitution |
| R3 | Indole | 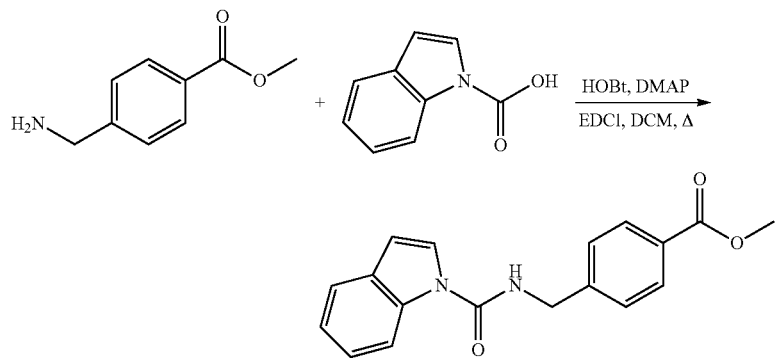 | Amide Coupling Reaction |
|  | Indoline | 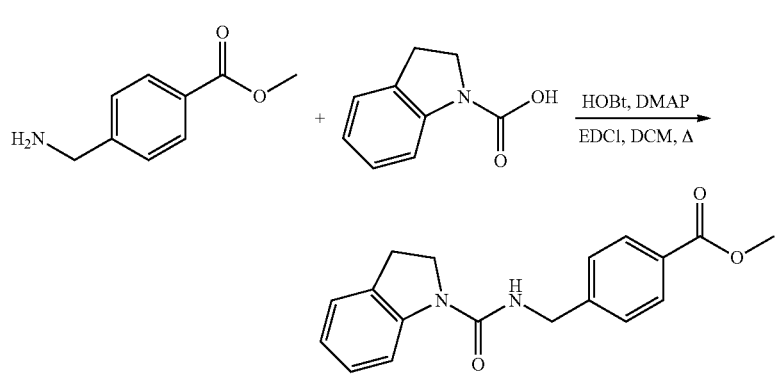 | Amide Coupling Reaction |

What is claimed is:

1. A compound of formula 1:

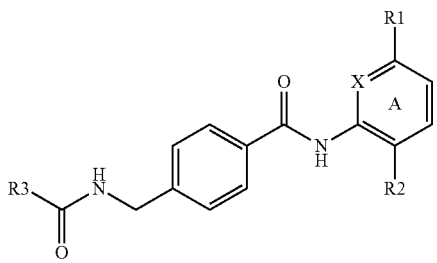

Formula 1 wherein R1 is phenyl or 4-fluorophenyl; R2 is an amino group (NH$_2$),

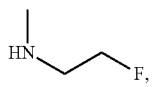

or

R3 is Indoline; X is C; A designates

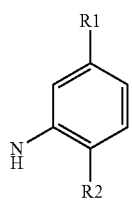

2. The compound of claim 1:
wherein the compound is of type INNO-IBM having symbols A, R1, R2, R3 as indicated below:

| Type | A | R1 | R2 | R3 |
|---|---|---|---|---|
| INNO-IBM | R1 substituted phenyl with NH-R2 | F-phenyl (4-F) | NH$_2$ | indoline |

3. The compound of claim 1,
wherein the compound is of type INNO-IBM-c having symbols A, R1, R2, R3 as indicated below:

| Type | A | R1 | R2 | R3 |
|---|---|---|---|---|
| INNO-IBM-c | R1 substituted phenyl with NH-R2 | phenyl (methyl) | HN-CH$_2$CH$_2$-F | indoline |

4. The compound of claim 1,
wherein the compound is of type INNO-IBM-d having symbols A, R1, R2, R3 as indicated below:

| Type | A | R1 | R2 | R3 |
|---|---|---|---|---|
| INNO-IBM-d | R1 substituted phenyl with NH-R2 | phenyl (methyl) | HN-CH$_2$-C≡C-F | indoline |

5. The compound of claim 1,
wherein the compound is of type INNO-IBM-f having symbols A, R1, R2, R3 as indicated below:

| Type | A | R1 | R2 | R3 |
|---|---|---|---|---|
| INNO-IBM-f | R1 substituted phenyl with NH-R2 | phenyl (methyl) | NH$_2$ | indoline |

6. The compound of claim 1 is selected from a group consisting of type INNO-IBM-i:
wherein the compound type INNO-IBM-i having symbols A, R1, R2, R3 is indicated below:

| Type | A | R1 | R2 | R3 |
|---|---|---|---|---|
| INNO-IBM-i | 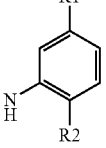 | 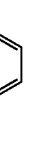 |  | 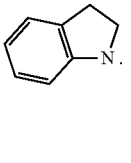 |
7. The compound of claim 1 is selected from a group consisting of type INNO-IBM-j:
   wherein the compound type INNO-IBM-j having symbols A, R1, R2, R3 is indicated below:
| Type | A | R1 | R2 | R3 |
|---|---|---|---|---|
| INNO-IBM-j | 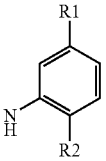 | 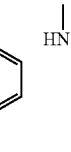 |  | 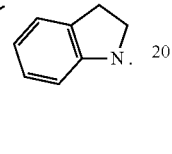 |
* * * * *